(12) United States Patent
Bernstein

(10) Patent No.: US 7,629,378 B2
(45) Date of Patent: Dec. 8, 2009

(54) COMPOSITIONS AND METHOD FOR TREATING AFFECTIVE, PAINFUL OR ALLERGIC DISORDERS

(75) Inventor: Joel E. Bernstein, Deerfield, IL (US)

(73) Assignee: Gideon Pharmaceuticals, Inc., Vernon Hills, IL (US)

( * ) Notice: Subject to any disclaimer, the term of this patent is extended or adjusted under 35 U.S.C. 154(b) by 895 days.

(21) Appl. No.: 10/781,254

(22) Filed: Feb. 18, 2004

(65) Prior Publication Data

US 2004/0167206 A1    Aug. 26, 2004

Related U.S. Application Data

(63) Continuation of application No. 10/294,409, filed on Nov. 14, 2002, now abandoned.

(51) Int. Cl.
*A61K 31/335* (2006.01)
(52) U.S. Cl. ..................... 514/450
(58) Field of Classification Search ............ 514/217, 514/278, 450, 656, 643
See application file for complete search history.

(56) References Cited

U.S. PATENT DOCUMENTS

| | | | |
|---|---|---|---|
| 4,370,324 A | 1/1983 | Bernstein |
| 4,395,420 A | 7/1983 | Bernstein |
| 4,505,909 A | 3/1985 | Bernstein |
| 4,636,125 A | 1/1987 | Burgard |
| 5,502,047 A | 3/1996 | Kavey |
| 6,096,738 A | 8/2000 | Bernstein |

FOREIGN PATENT DOCUMENTS

| | | |
|---|---|---|
| CA | 1177406 | 11/1984 |
| CA | 1185179 | 4/1985 |
| CA | 1198059 | 12/1985 |

OTHER PUBLICATIONS

Arzneim-Fosch; "Plasma Levels of the Cis-and Trans-Isomers of Doxepin and Desmethyldoxepin after Administration of Doxepin tp Patents", Drug Res.31, vol. 1, pp. 113-115, 1981.
USP25, 2002; United States Pharmacopeia Convention, Inc. Rockville, MD, p. 614.
Midha et al., "Steroselective pharmacokinetics of doxepin isomers.", European Journal of Clinical Pharmacology (1992), 42(5), pp. 539-544.
Otsuki et al., "Comparison of Pharmacological Activities of Doxepin Hydrochloride with Its Geometrical Isomers," *Oyo Yakuri*, 6 (5): 973-984 (1972) (Abstract).
Pinder et al., "Doxepin Up-to-date: A Review of its Pharmacological Properties and Therapeutic Efficacy with Particular Reference to Depression," *Drugs*, 13: 161-218 (1977).
Ross, CRC Handbook of Stereoisomers: Drugs in Pharmacology, "*Antidepressant Drugs: (Z)- and (E)-Isomers*," CRC Press, Boca Raton, Fla., pp. 243-255 (1984).
Yan et al., "Absolute bioavailability an stereoselective pharmacokinetics of doxepin," *Xenobiotica*, 32 (7): 615-623 (2001).
International Search Report issued in PCT/US2003/36600 (2004).
Page 1 of Office Action issued in GB2411356 (2005).

*Primary Examiner*—Jennifer M Kim
(74) *Attorney, Agent, or Firm*—Barnes & Thornburg LLP; Alice O. Martin

(57) ABSTRACT

Therapeutic compositions of doxepin and having a preponderance of the cis doxepin isomer over the trans doxepin isomer provide therapeutic effects for affective, painful, or allergic disorders without the sedative effects commonly experienced with compositions having a preponderance of the trans doxepin isomer.

14 Claims, No Drawings

COMPOSITIONS AND METHOD FOR TREATING AFFECTIVE, PAINFUL OR ALLERGIC DISORDERS

This is a continuation application of, commonly-owned patent application Ser. No. 10/294,409, filed Nov. 14, 2002 now abandoned.

BACKGROUND OF THE INVENTION

Doxepin hydrochloride is a tricyclic compound most frequently used to treat the affective disorders depression and anxiety, but also less commonly employed as a secondary or tertiary treatment modality for a variety of painful (e.g. headache and neuropathic pain) and allergic (e.g. urticaria) disorders. While doxepin is generally recognized as effective for the treatment of such disorders, its use is limited by the systemic side effects associated with its ingestion or topical application. Principal among the systemic side effects accompanying doxepin administration, and most limiting to its usefulness as a drug, is sedation which occurs in from 20% to over 60% of subjects depending upon dosage and route of doxepin administration. According to USP 25,2000. United States Pharmacopeial Convention, Inc., Rockville, Md. p. 614, doxepin hydrochloride U.S.P. is a geometric isomer mixture "containing not less than 13.6% and not more than 18.1%" of this cis isomer and "not less than 81.4% and not more than 88.2%" of the trans isomer.

In an attempt to discover a compound that might have similar effectiveness to doxepin hydrochloride U.S.P. but less associated sedation, the applicant has evaluated the cis isomer, which as mentioned above constitutes less than 18.1% of doxepin hydrochloride. Applicant has discovered that cis doxepin hydrochloride, while purportedly more potent than doxepin hydrochloride U.S.P. in animals, quite surprisingly produces substantially less sedation at therapeutically effective dosages. The invention includes pharmaceutical compositions of cis doxepin suitable for administration to patients with affective disorders, painful disorders, or allergic disorders.

DETAILED DESCRIPTION OF THE PREFERRED EMBODIMENT

In accordance with the invention, formulations are provided that incorporate a preponderance of the cis doxepin isomer over the trans isomer into pharmaceutically acceptable vehicles suitable for use in human patients. Such formulations include those for application to the skin, such as solutions, creams, ointments, gels, lotions, or pastes. Such formulation also include those for application to mucous membranes, including ophthalmic and nasal solutions and solutions and suspensions, suppositories, and plasticized formulations suitable for oral and vaginal applications. Cis doxepin may also be formulated in sterile solutions or suspensions suitable for intradermal, subcutaneous, intramuscular, intravenous, or cerebrospinal injection. In each of the foregoing formulations, whether for application to the skin, application to the mucous membranes, or for injection, the cis doxepin isomer may be present in the amount of about 0.01% to about 10% by weight, and preferably about 0.05% to about 5% by weight, and any trans doxepin isomer that may be present is in an amount less than that of the cis doxepin isomer.

Formulations within the scope of the invention also includes those suitable for oral administration such as capsules, tablets, or liquid solutions or suspensions. In such formulations, the cis doxepin isomer may be present in amounts of about 0.5-500.0 mg, and preferably about 1.0-50.0 mg, per tablet, capsule, or 5 ml dose of liquid solution or suspension; and any trans doxepin isomer that may be present is in an amount less than that of the cix doxepin isomer.

Suitable pharmaceutical vehicles for the cis doxepin formulations of the instant invention, whether for topical application to skin or mucous membrane, injection, or oral administration, and methods of preparing such formulations as are within the scope of the invention, will be readily apparent to and understood by those skilled in the art.

The instant invention also comprises the method of applying, instilling, injecting, ingesting, or inhaling medicinal formulations containing a preponderance of the cis doxepin isomer over the trans doxepin isomer in order to treat a wide range of affective, painful, and/or allergic disorders of man and animals such as depression, anxiety, migraine headache, tension headache, neuralgia, urticaria, allergic rhinitis, and pruritic disorders of the skin.

The compositions of the instant invention and the methods of their use will be more readily comprehended from the following examples.

EXAMPLES

The formulations used in the following examples were made using a cis doxepin composition prepared by Sigma Aldrich, Inc. of Sheboygan, Wis., the composition comprising not less than about 85% of the cis-isomer, with the balance of the composition being the trans-isomer. Amounts of cis doxepin as stated in the examples are the actual amounts of the cis doxepin isomer in each formulation.

Example 1

Cis doxepin isomer is incorporated into hard gelatin capsules in a dosage of 10 mg/capsule, and is administered once or twice daily to patients with acute or chronic urticaria in order to prevent new urticarial lesions.

Example 2

A cream containing cis doxepin isomer 1.0% by weight is applied two to four times daily to pruritic skin lesions by patients with atopic dermatitis. Application of this cream provides for relief of itching as well as more prompt resolution of the skin lesions without producing the incidence or severity of sedation observed with application of prior art doxepin containing creams in which the trans isomer is predominant.

Example 3

An aqueous solution of 0.2% by weight of the cis doxepin isomer is administered by nasal spray to the noses of patients with allergic rhinitis to treat and prevent nasal stuffiness.

Example 4

An aqueous solution of 0.1% by weight of the cis doxepin isomer is applied to the eyes of patients with allergic conjunctivitis to relieve symptoms of eye irritation.

Example 5

Suppositories containing 20 mg by weight of the cis doxepin isomer in a hydrogenated coglyceride base are inserted rectally twice to three times daily for relief of pain and/or itching in patients with proctitis or pruritis ani.

Example 6

Cis doxepin is incorporated into tablets containing 50 mg by weight of the cis doxepin isomer and such tablets are administered orally once to four times daily to patients with affective disorders so as to relieve feelings of depression or anxiety without producing substantial sedation in such patients.

While the foregoing is a description of the preferred embodiments of the instant invention it will be readily apparent to those skilled in the art that various modifications may be made therein without departing from the true scope and spirit of the invention as set forth in the appended claims.

The invention claimed is:

1. A composition comprising a preponderance of cis doxepin isomer over trans doxepin isomer, said cis doxepin isomer being present in an amount of about 0.01% to about 10.0% by weight, and a pharmaceutically acceptable vehicle, said composition for use in the treatment of affective, painful, allergic disorders, said composition being comparable in efficacy to compositions containing a preponderance of the trans doxepin isomer but with significantly less sedative effects.

2. The composition of claim 1 wherein said composition is suitable for application to the skin.

3. The composition of claim 2 wherein said vehicle is selected from the group consisting of a lotion, a solution, a cream, an ointment, a gel, or a paste.

4. The composition of claim 1 wherein said composition is suitable for application to mucous membranes.

5. The composition of claim 4 wherein said vehicle is selected from the group consisting of solutions, suspensions, suppositories, and plasticized formulations.

6. The composition of claim 1 wherein said composition is suitable for injection.

7. The composition of claim 1 wherein said cis doxepin isomer is present in the amount of about 0.05% to about 5.0% by weight.

8. A method of treating affective, painful or allergic disorders comprising treatment with an effective amount of a composition containing a preponderance of cis doxepin isomer over trans doxepin isomer, said cis doxepin isomer being present in an amount of about 0.01% to about 10.0% by weight in a pharmaceutically acceptable vehicle, said composition being comparable in efficacy to compositions containing a preponderance of the trans doxepin isomer but with significantly less sedation.

9. The method of claim 8 wherein said method of treatment is selected from the group consisting of application to skin, application to mucous membranes and injection.

10. The method of claim 8 wherein said cis doxepin isomer is present in the amount of about 0.05-5.0% by weight.

11. A composition suitable for oral administration comprising a pharmaceutically acceptable vehicle in the form of capsules, tablets, liquid solutions or suspensions and containing a preponderance of cis doxepin isomer over trans doxepin isomer, said cis doxepin isomer present in an amount of about 0.5-500.0 mg per capsule, tablet or 5 ml portion of liquid, said composition being comparable in efficacy to compositions containing a preponderance of the trans doxepin isomer but with significantly less sedative side effects.

12. The composition of claim 11 wherein said cis doxepin isomer is present in the amount of about 1.0-50.0 mg per capsule, tablet, or 5 ml portion of liquid.

13. A method of treating affective, painful, or allergic disorders by oral administration and comprising treatment with an effective amount of a composition containing a preponderance of cis doxepin isomer over trans doxepin isomer, said cis doxepin isomer being present in an amount of about 0.5-500.0 mg per dose or 5 ml portion of liquid in a pharmaceutically acceptable vehicle, said composition being comparable in efficacy to compositions containing a preponderance of trans doxepin isomer but with significantly less sedative side effects.

14. The method of claim 13 wherein said cis doxepin isomer is present in the amount of about 1.0-50.0 mg per dose.

\* \* \* \* \*